United States Patent [19]

Kirsch

[11] Patent Number: Plant 6,175

[45] Date of Patent: May 10, 1988

[54] LILY PLANT NAMED TUMALO

[75] Inventor: Ted T. Kirsch, Myrtle Point, Oreg.

[73] Assignee: Melridge Inc., Gresham, Oreg.

[21] Appl. No.: 861,246

[22] Filed: May 8, 1986

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Charles W. Rummler; W. Dennis Drehkoff

[57] ABSTRACT

A new and distinct variety of Oriental hybrid lily characterized particularly by its very short stature and its large, outwardly and generally upwardly facing flowers having an unusual overall pattern of a generally red-purple color with a more peach-toned stripe along each tepal midrib, and being copiously marked over a major portion of its area with papillae of a dark spiraea red color, this plant also having a compact and vigorous growth habit with good strength and abundant foliage.

1 Drawing Sheet

BACKGROUND OF THE INVENTION

This new lily plant originated as a seedling of unknown parentage discovered by me at my nursery in Arcata, Calif., and I was particularly attracted by its combination of very short stature and large, richly colored flowers which presented a subject that could be very appropriate for a pot plant cultivar and with that in mind, I proceeded to propagate this plant for testing and further evaluation. My propagation of this plant by natural propagation from bulblets indicated that this new plant would retain its short habit, broad leaves and large flower size under further asexual propagation and this was done by me and also under my direction at Arcata, Calif. Successive generations produced by bulb scale propagation, natural propagation from bulblets and division, as well as by tissue culture propagation originating from bulb scales, demonstrated conclusively that the novel and distinctive characteristics of this plant would hold true under asexual propagation from generation to generation and appeared to be firmly fixed. Further testing and observation demonstrated that the bulbs of this plant, when dug at the proper stage of maturity and when they are properly precooled, can be forced into flower out-of-season with reliable performance even during periods of relatively low light and the resulting plants continue to retain the short habit, broad leaves, large flower size and good bud color of the parent plant.

DESCRIPTION OF THE DRAWING

My new variety of lily plant is illustrated by the accompanying photographic drawing in which the upper view shows buds and a full face view of a mature flower, and in the lower view, a three-fourths face view of the flower to illustrate its bowl shape and more particularly the arrangement of its tepals, the color rendition being as nearly true as can be reasonably obtained by conventional photographic procedures.

DESCRIPTION OF THE NEW VARIETY

The following is a detailed description of my new variety of Oriental hybrid lily, with nomenclature according to The International Lily Register (The Royal Horticultural Society, London, 1969) and with color designations according to The R.H.S. Colour Chart published in 1966. These observations were made on field grown plants from Arcata, Calif., in the summer of 1985.

THE PLANT

Origin: Seedling.

Parentage: Unknown.

Classification:

- *Botanic.*—Hybrid Lilium Cultivar; Division VII-B of The Horticultural Classification of Lilies by The Royal Horticultural Society.
- *Commercial.*—Oriental Hybrid Lily.

Form: Single stem, erect and bushy.

Height: About 40 to 50 cm.

Growth: Vigorous and compact with good strength.

Foliage:

- *Quantity.*—Abundant.
- *Leaf size.*—Ranging from about 10 cm. long and 2 cm. wide at the top of the stem to about 5 cm. long and 2 cm. wide at the bottom of the foliage growth.
- *Leaf shape.*—Broad lanceolate.
- *Texture.*—Leathery.
- *Aspect.*—Glossy.
- *Color.*—Dark green, the chlorophyll pigmentation being overlaid with light anthocyanin.

Bulbs:

- *Size.*—Varying up to about 30 cm. in circumference, depending upon age.
- *Color.*—White, with flushes of soft pink or yellow which deepen as the bulbs become larger or are exposed to light.

THE BUD

Form: Generally ovate urn-shaped with obtuse apex.

Size: About 10 cm. long and 10 cm. in circumference, depending upon light and nutritional levels.

Opening rate: The bud opens slowly, in response to morning light, and the buds open successively from the lowermost to the uppermost as is typical of Lilium.

Color: White to softest pink with ribs of light yellow-cream at the apical end and slightly green at the basal end.

Peduncle:

- *Length.*—Usually very short and less than 1 cm.; the peduncle may elongate somewhat under low light conditions or when the bulbs have been improperly stored prior to forcing.

THE FLOWER

Blooming habit: This plant flowers once and profusely in midseason, generally in late July under field conditions at Arcata, Calif. When the bulbs are properly forced after being appropriately precooled, this plant will flower in 95 to 110 days in the greenhouse.

Size of flower: Large; flowers average about 20 cm. in diameter with tepals recurving to form a bowl of about 16 cm. wide and about 5 to 7 cm. deep.

Borne: As a compact raceme with each pedicel having one bud and the bulbs of typical commercial size will produce an average of about five to eight flowers.

Shape: Bowl-shaped, with broad, hexagonally arranged tepals, slightly recurved.

Tepalage:

*Number.*—Six.

*Arrangement.*—Hexagonal with inner tepals uniformly related angularly with the narrower outer tepal.

*Form.*—The inner tepals are broadly ovate with acute bases and generally acuminate tips, the inner tepals averaging about 5 cm. wide and the outer tepals averaging about 3 cm. wide.

*Color.*—The basic color of the tepals is in the nature of orchid pink in the Red Purple Group of 62C, with a more peach tone color of 38A 10 to 15 mm. wide along the tepal midrib, the basic color shading through 62C to 63C along the outer margins. The tepal margins are slightly frilled and the papillae are 63B. The nectaries are green with a 2 to 4 mm. wide yellow margin.

*Tepal longevity.*—The tepals stay on the stem about two to three weeks.

*Color change.*—The color fades slightly and becomes more brown as the flower ages, or in intense light and heat. Under cool conditions, the color is richer and is retained longer.

Pedicel:

*Length.*—About 3 to 5 cm.

*Color.*—Dark green.

*Character.*—Ascending at an angle of about 45° from the stem.

Disease resistance: The flower and plant are adequately resistant to disease as observed in northwestern California and western Oregon.

Fragrance: The fragrance is heavy and sweet.

Lasting quality: The flower is long lasting, both on field grown plants and on forced potted cultivars.

REPRODUCTIVE ORGANS

Stamens:

*Number.*—Six.

*Arrangement.*—Typical of Lilium.

Anthers:

*Color.*—172A-B.

Filaments:

*Length.*—About 7 to 8 cm.

*Color.*—Light green.

Pistil:

*Number.*—One per flower.

Style:

*Color.*—Light green.

Stigma:

*Size.*—About 5 to 6 mm. wide.

*Color.*—Soft purple-grey.

Ovary: Typical of genus Lilium.

I claim:

1. A new and distinct variety of Oriental hybrid lily, substantially as herein shown and described, particularly characterized by its outfacing pink flowers of large size and by its short stature, the flowers being of good substance and form and distinctively marked with a peach-toned stripe extending along the tepal midribs, and being copiously marked with dark red papillae over a major portion of the tepal length, this plant having abundant foliage of broad leaves of a dark green color and the flowers being carried as a raceme on ascending pedicels.

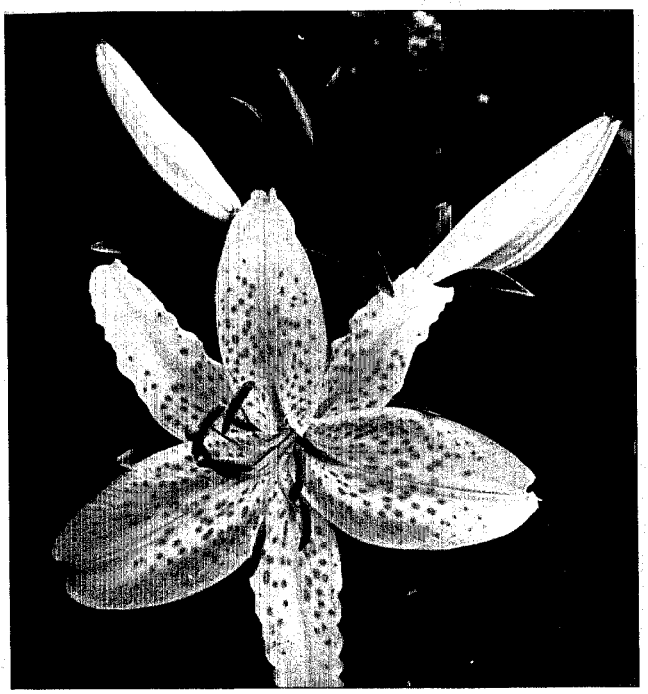
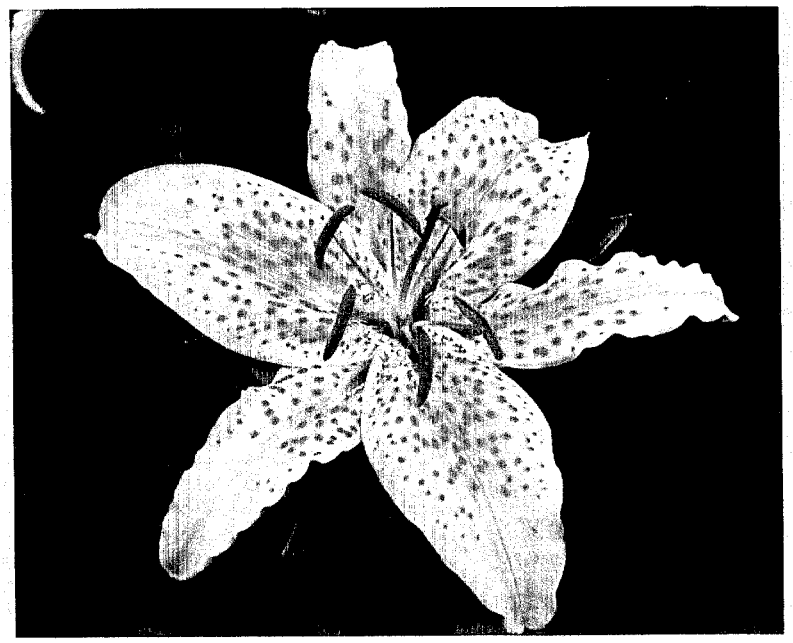

* * * * *